United States Patent [19]
Cavallari

[11] 4,193,293
[45] Mar. 18, 1980

[54] APPARATUS FOR DETERMINING BLOOD ELASTICITY PARAMETERS

[75] Inventor: Francesco Cavallari, Milan, Italy

[73] Assignee: E.L.V.I. S.p.A., Milan, Italy

[21] Appl. No.: 900,057

[22] Filed: Apr. 25, 1978

[30] Foreign Application Priority Data

Apr. 28, 1977 [IT] Italy ................ 22920 A/77

[51] Int. Cl.² ........................... G01N 33/16
[52] U.S. Cl. ........................... 73/64.1
[58] Field of Search ............... 73/64.1, 59

[56] References Cited

U.S. PATENT DOCUMENTS

| 3,714,815 | 2/1973 | Hartert ............... 73/64.1 |
| 4,148,216 | 4/1979 | Do et al. ............ 73/64.1 X |

FOREIGN PATENT DOCUMENTS

| 2227943 | 12/1973 | Fed. Rep. of Germany ........ 73/64.1 |
| 325965 | 3/1972 | U.S.S.R. .......................... 73/64.1 |
| 368858 | 4/1973 | U.S.S.R. .......................... 73/64.1 |
| 513686 | 7/1976 | U.S.S.R. .......................... 73/64.1 |

*Primary Examiner*—Gerald Goldberg
*Assistant Examiner*—Joseph W. Roskos
*Attorney, Agent, or Firm*—Fleit & Jacobson

[57] ABSTRACT

Apparatus for determining blood elasticity parameters, comprising a cylinder suitable to be immersed in a blood container subjected to regular oscillations. The cylinder is rigidly secured to a frame oscillating according to a vertical axis and mechanically connected to an electromagnetic device generating a reaction force; the frame is also connected to a linear electromagnetic transducer suitable to supply signals to a thromboelastogram recording apparatus.

8 Claims, 1 Drawing Figure

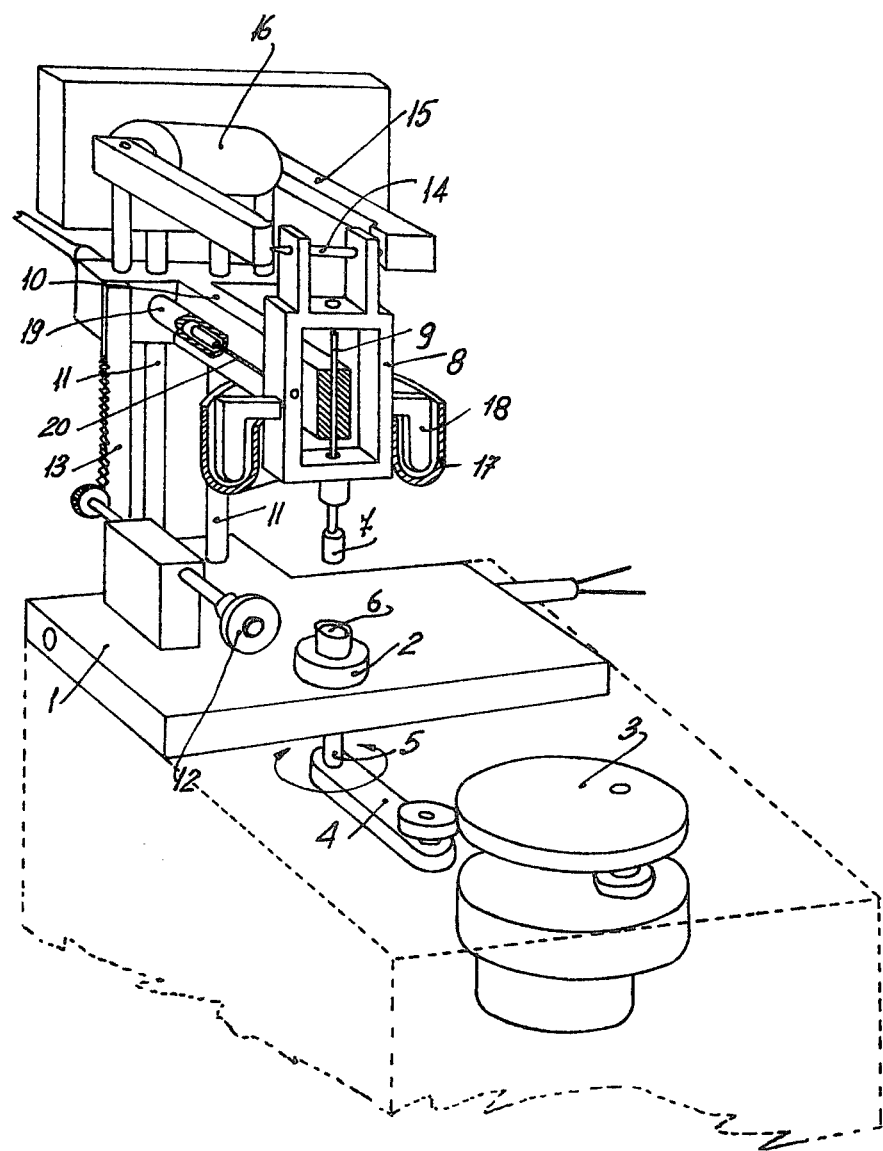

APPARATUS FOR DETERMINING BLOOD ELASTICITY PARAMETERS

This invention relates to an apparatus for determining blood elasticity parameters by establishing a characteristic curve for the blood coagulation process, such an apparatus being normally referred to as thromboelastograph.

It is well known that among the various types of blood analysis, that type of blood analysis is popular provides which allows so-called thromboelastograms, which are obtained by photographic or optical-mechanical processes.

In such known apparatus, the periodical angular deviation is established for a cylinder immersed in a blood container subjected to regular oscillations. Such a cylinder is suspended from a calibrated metal cable secured at its upper end to provide a resisting or reacting moment to the cylinder rotations. As blood coagulation proceeds in the container, the cylinder will increasingly give oscillation to the container according to a law, which is true for small angles as in this case, until a balanced condition is achieved between the torsional torque exerted on the cylinder by the blood being coagulated and the resisting moment resulting from the torsion of the metal cable supporting said cylinder. An optical transducer, such as a mirror impinged on by a light beam, or a magnetic transducer, is directly or indirectly connected to the cylinder for conversion of oscillations thereof in signals which can be suitably recorded on a proper recording apparatus. Thus, the cylinder oscillation amplitude is recorded to acknowledge the progress of blood coagulation progress, whereby the thromboelastogram is obtained.

The known apparatus described above suffer from a number of disadvantages, the most serious of which is due to the practical impossibility of providing cylinder supporting cables fully identical to one another. Thus, each cable in accordance with both its geometrical configuration the nature of the material being used has its own torsional characteristics which, along with the practical impossibility of accurately calibrating said cylinder supporting cables, renders it highly difficult to obtain identical thromboelastograms from apparently like apparatus, whereby the analyses to be performed would be seriously impaired.

Additionally, since the cable suspended cylinder should be immersed in and removed from the blood container every time that an analysis is carried out, provision of the delicate cylinder supporting cable is difficult because of the risk that the thin cable may be deformed or damaged, thereby rendering the apparatus unusable. In addition, the cost of such cables is very high.

It is the object of the present invention to provide an apparatus of the above specified character, wherein the aforesaid disadvantages are completely overcome owing to a novel supporting and reacting system for the cylinder to be immersed in the blood container.

Generally, according to the invention, an apparatus for determining blood elasticity parameters comprises a cylinder rigidly suspended from an oscillating frame according to the axis of the cylinder and mechanically connected to a magnetic reaction device comprising a ferromagnetic core rotating in a uniform magnetic field.

According to a preferred embodiment, the ferromagnetic core is rigidly secured to the cylinder carrying frame so as to rotate in a plane perpendicular to the axis of the cylinder. Thus, the angular rotations of the ferromagnetic core suitably correspond to the small angular rotations of the cylinder, with respect to the direction of the magnetic field, providing a resisting moment proportional (for small angles as in the present case) to the angle of rotation until reaching a balanced condition with the torsional torque exerted on the cylinder by the coagulating blood. The constant of proportionality depends on the strength of such a field and shape of the ferromagnetic core. Therefore, the magnetic field is advantageously built up by the pole pieces of an electromagnet, which are so shaped that the magnetic field is not significantly disturbed by the provision of the ferromagnetic core rotating between said pole pieces, and such to afford an adjustment of the field strength by adjusting the electric current.

These and further features of the apparatus according to the present invention will be hereinafter illustrated with reference to the FIGURE of the accompanying drawing schematically showing the subject apparatus.

As shown in said FIGURE, the apparatus comprises a supporting structure 1 defining a plane having thereon a plate 2 rotable about a vertical axis for oscillation, with periodical angular rotations varying up to 4.15°, for example by means of a cam control system 3 operated by an electric motor, a belt drive 4, and a shaft 5 connected to said plate 2.

A blood container 6, in which a cylinder 7 can be immersed and removed, is located on said oscillating plate 2.

Cylinder 7 is rigidly suspended from a frame 8 capable of rotating and oscillating without any friction on a mounting rod 9 secured to a horizontal arm 10, which can slide along vertical guides 11 and be secured in place by acting on a flywheel 12 causing a sliding movement of a rack 13 integral with said arm 10.

In order to minimize the rolling friction between said frame 8 and mounting rod 9, the latter is made with conical or tapered ends having the frame pins bearing thereagainst comprising hardened screws at the head provided with a hard stone, such as synthetic jewels and the like, having a substantially negligible coefficient of rolling friction.

Moreover, said cylinder carrying frame 8 has a ferromagnetic core 14 secured thereto and arranged with its axis perpendicular to the axis of rotation of cylinder 7. This core 14 rotates in an even magnetic field provided between the pole pieces of a magnetic circuit 15 linked with a coil 16 having a current passing therethrough.

In the case shown, coil 16 of the relevant magnetic circuit 15 is supported by arm 10 and moves vertically therewith. However, if desired, said magnetic circuit 15 and coil 16 could have an installation fixed to structure 11 or a structure associated therewith.

Magnetic core 14 immersed in the field generated by magnetic circuit 15, 16 forms a magnetic reaction device providing a resisting moment or torque for the cylinder 7 proportional to the angle of rotation of said cylinder. Since the strength of the magnetic field can be varied by simply varying the intensity of the current flowing through coil 16, a calibration can be thus obtained for the constant of proportionality between the cylinder angle of rotation and the resisting moment exerted by the electromagnetic device above disclosed. Thus, the construction of apparatuses can be assured for determining the blood elasticity parameters, capable of providing identical thromboelastograms within limits of close determination.

Cylinder carrying frame 8 has also associated therewith an oleodynamic damper comprising a basin 17 containing a suitable liquid, such as oil, in which tabs 18 integral with frame 8 rotate.

The recording of a thromboelastogram is provided by converting the rotations of cylinder 7 in suitable signals obtained, for example, by a mirror associated with said frame, on which a light beam is made to be incident or, as shown, by a linear electromagnetic transducer 19, the movable core or plunger of which is connected through a rod 20 to one side of frame 8. This transducer 19 is electrically connected with a conventional processing and recording apparatus (not shown) supplying a graphic indication of the thromboelastogram. The use of such a linear transducer, based on changes in magnetic reluctance (differential transformer) is important because it directly provides electrical signals proportional to the angular deviations of the cylinder. This allows a processing thereof by means of suitable electronic analog or digital processors for directly providing (in actual time) the parameters distinguishing the thromboelastographic analysis, without having to resort to graphic recording of the thromboelastogram and study of its distinguishing parameters. In order that the rotating core should not in the least alter the magnetic field, such a core must be of a reduced section relative to that of the pole pieces. Excellent results were obtained by pole pieces of square cross-section with a side of 13 mm and an interspacing of 18 mm, while core 14 has a maximum diameter of 2.5 mm and a maximum length of 15 mm.

From the foregoing and as shown on the accompanying drawing, the use and operation of the apparatus would be apparent, as hereinafter summarized. Under rest or inoperative conditions, when no electric current flows through coil 16, the rotor or rotating element of the magnetic reaction device can freely rotate allowing, when lifted by an upward movement of arm 10, a suitable start and analysis operations. Then, upon building up of the magnetic field, the whole rotor or rotating element takes a central position due to the action exerted on core 14 of said magnetic field. Such a position can be varied upon checking, for example, by simply rotating the electromagnet.

As soon as an even minimal angular deviation of cylinder 7 occurs under the action of the torque exerted by the blood coagulating within container 6, said magnetic core 14 rotates along with the whole rotor or rotating element forming an angle with the direction of the magnetic field which is fixed in the space. Thus, a resisting moment is built up, which is substantially proportional to said angular deviation, due to the negligible magnitude of the rolling frictions being applied to the rotor or rotating element of the magnetic reaction device.

Cylinder 7 will continue to rotate, for example in a clockwise direction, until the rates of torque and resisting moment become equal. When the blood container starts to rotate again the opposite direction, it will draw along the cylinder and whole rotor or rotating element of the electromagnetic reaction device similarly and symmetrically as before. Transducer 19 associated with cylinder 7 provides for recording the angular deviations of the cylinder, which will be suitably recorded and converted in the desired thromboelastogram, which may be accordingly analyzed by the operator.

Therefore, from the foregoing and as shown, it will be appreciated that the particular embodiment of the rotor or rotating element for the magnetic reaction device extremely facilitates all the operations as required for the actual analysis, such as lifting of the rotor or rotating element and cylinder and removal and cleaning of the blood container, without impairing or altering the features of the apparatus.

Details of construction of the apparatus may be substantially varied, without departing from the solution concept as herein shown.

What we claim is:

1. An apparatus for determining blood elasticity parameters, comprising in combination: a cylinder rotatably carried about its vertical axis and suitable to be immersed in a blood container subjected to regular oscillations; a magnetic transducer for the cylinder oscillations connectable to an apparatus for recording the amplitude of the cylinder oscillations; the cylinder being rigidly suspended from a frame oscillating in line with the cylinder axis and being mechanically connected to a magnetic device exerting a reaction moment, said device comprising a ferromagnetic core rotating in a uniform magnetic field.

2. An apparatus according to claim 1, in which said cylinder, frame and at least the ferromagnetic core of the reaction device are carried by a mounting or support adjustable in height.

3. An apparatus according to claim 1, in which said frame is connected to a damper for the rotations of the frame.

4. An apparatus according to claim 1, in which said ferromagnetic core is secured at the top to said frame at a position perpendicular to the cylinder axis of rotation.

5. An apparatus according to claim 1, in which the magnetic field is generated by an adjustable electromagnetic device.

6. An apparatus according to claim 1, in which said transducer is a linear electromagnetic type of transducer.

7. An apparatus according to claim 2 in which:
(A) said frame is connected to a damper for the rotations of the frame;
(B) said ferromagnetic core is secured at the top to said frame at a position perpendicular to the cylinder axis of rotation;
(C) said magnetic field is generated by an adjustable electromagnetic device; and
(D) said transducer is a linear electromagnetic type of transducer.

8. An apparatus according to claims 1 or 7 connected to an apparatus for recording the amplitude of the cylinder oscillations.

* * * * *